United States Patent
Richard et al.

(10) Patent No.: US 9,206,204 B2
(45) Date of Patent: Dec. 8, 2015

(54) PROCESS FOR PREPARING 2-HYDROXYPHENYL BENZOTRIAZOLE SILOXANE COMPOUNDS

(75) Inventors: Herve Richard, Gagny (FR); Patricio Guerreiro, Avilly-Saint-Leonard (FR); Jianping Guo, Jiangxi (CN); Wensheng Tang, Shanghai (CN)

(73) Assignee: L'OREAL, Paris (FR)

( * ) Notice: Subject to any disclaimer, the term of this patent is extended or adjusted under 35 U.S.C. 154(b) by 303 days.

(21) Appl. No.: 13/814,592

(22) PCT Filed: Oct. 25, 2010

(86) PCT No.: PCT/CN2010/001672
§ 371 (c)(1),
(2), (4) Date: Mar. 19, 2013

(87) PCT Pub. No.: WO2012/055064
PCT Pub. Date: May 3, 2012

(65) Prior Publication Data
US 2013/0204006 A1  Aug. 8, 2013

(51) Int. Cl.
*C07F 7/08* (2006.01)
*C07D 249/20* (2006.01)

(52) U.S. Cl.
CPC ............ *C07F 7/0879* (2013.01); *C07D 249/20* (2013.01); *C07F 7/0849* (2013.01)

(58) Field of Classification Search
CPC .................................................... C07F 7/0879
See application file for complete search history.

(56) References Cited

U.S. PATENT DOCUMENTS

| | | | |
|---|---|---|---|
| 5,089,250 A * | 2/1992 | Forestier et al. ................ | 424/43 |
| 5,618,520 A | 4/1997 | Hansenne et al. | |
| 6,409,999 B2 | 6/2002 | Agostini et al. | |
| 6,627,179 B2 | 9/2003 | Candau | |

FOREIGN PATENT DOCUMENTS

| | | | |
|---|---|---|---|
| CN | 1310607 | 8/2001 | |
| CN | 1425366 | 6/2003 | |
| FR | 2 818 143 | 6/2002 | |
| WO | 94 06404 | 3/1994 | |
| WO | WO 94/06404 | * 3/1994 | ............... A61K 7/42 |

OTHER PUBLICATIONS

International Search Report Issued Aug. 4, 2011 in PCT/CN10/01672 Filed Oct. 25, 2010.
U.S. Appl. No. 13/814,539, filed Feb. 6, 2013, Richard, et al.

* cited by examiner

*Primary Examiner* — Joseph Kosack
(74) *Attorney, Agent, or Firm* — Oblon, McClelland, Maier & Neustadt, L.L.P.

(57) ABSTRACT

A process for preparing a siloxane compound comprising a 2-hydroxyphenyl benzotriazole function which comprises at least one step in which a reaction for hydrosilylation of a compound 2-hydroxyphenyl benzotriazole comprising a substituent having a terminal double bond with a siloxane compound comprising an SiH function is carried out in the presence of a catalyst and of at least one volatile organic solvent corresponding to one of formula (VII) or (VIII). in which $R_4$ and $R_5$, which may be identical or different, represent a linear or branched $C_1$-$C_4$ alkyl radical, with the proviso that the sum of the carbons of $R_4$ and $R_5$ is less than or equal to 6; y is and integer between 1 and 3; $R_6$ which may be identical or different, are linear or branched $C_1$-$C_3$ alkyl radicals, with the proviso that the sum of the carbons of $R_6$ is less than or equal to 6 is disclosed.

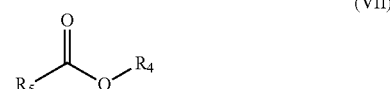

(VII)

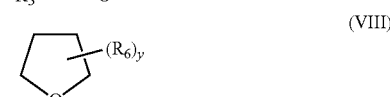

(VIII)

20 Claims, No Drawings

PROCESS FOR PREPARING 2-HYDROXYPHENYL BENZOTRIAZOLE SILOXANE COMPOUNDS

The present invention relates to a process for preparing 2-hydroxyphenyl benzotriazole siloxane compounds in particular of formula (III) which will be defined later in detail.

Light radiation with wavelengths between 280 nm and 400 nm is known to brown the human epidermis; more particularly, rays with a wavelength between 280 and 320 nm, known as UV-B rays, are known to be possibly harmful to the development of a natural tan. For these reasons and for aesthetic reasons, there is a constant demand for means for controlling this natural tanning which can thereby control the colour of the skin; it is therefore advisable to screen out this UV-B radiation.

It is also known that UV-A rays with wavelengths between 320 and 400 nm, which cause the skin to brown, are capable of inducing alterations in said skin, in particular in the case of sensitive skin or of skin continually exposed to solar radiation. UV-A rays in particular cause a loss of elasticity of the skin and the appearance of wrinkles, resulting in premature ageing of the skin. Thus, for aesthetic and cosmetic reasons, such as preserving the natural elasticity of the skin for example, more and more people would like to control the effect of UV-A rays on their skin. It is therefore desirable to also screen out UV-A radiation.

With the aim of providing the skin and keratin materials with protection against UV radiation, anti-sun compositions comprising organic or inorganic screens active in the UV-A range and active in the UV-B range are generally used.

Many industrial sectors outside the cosmetics industry also have recourse to the use of UV screens for providing photoprotection for various materials against UV radiation, and in particular solar radiation.

This is in particular the case of protective coating, ink or paint formulations intended to be applied to products which are continually exposed to UV radiation, such as construction materials, materials used in the motor vehicle industry, or packaging plastics. For these colouring formulations, UV screens which are transparent, photostable, compatible with the usual ingredients contained in such formulations and effective in terms of resistance to light of the desired colour are most particularly sought.

This is also the case of polymer compositions used in particular in the manufacture of plastics which are stable during storage, where the desire is for UV radiation-screening agents that are particularly suitable for the processes for manufacturing and transforming the polymers, which must in particular exhibit good resistance at high temperatures for extrusion.

In the natural-fibre, artificial-fibre or synthetic-fibre textile industry, the desire is for broad-spectrum photostable UV screens which are compatible with the processes for manufacturing said fibres, in particular in the case of the manufacture of polyamide fibres, such as nylon, which are resistant to high temperatures and make it possible to integrate UV protection during extrusion. UV screens which exhibit good affinity and good adhesion to the fibres, thus allowing them in particular to have good resistance to successive rounds of washing, are also sought. The UV screens sought should also allow good-protection both of the textile fibres and also of the skin and other human keratin materials in contact with said fibres.

Similar problems also arise in the manufacture of paper generally made of cellulosic fibres, in which the UV screens used should also be photostable, transparent and compatible with the other customary ingredients and suitable for the various paper manufacturing techniques.

The industry producing mineral or organic glasses, and in particular glasses used in ophthalmology, is looking for UV screens which should have a broad spectrum (active in the UVA range and in the UVB range), and which are photostable, transparent and compatible with the various techniques for treating glasses, for instance the process of attachment to the glass matrix or the application of a photoprotective coating, for example in the case of polycarbonate glasses.

A particularly advantageous family of organic screens which have absorbent properties in both the UVA range and the UVB range is made up of the 2-hydroxyphenyl benzotriazole siloxane compounds.

The term "siloxane compound comprising a 2-hydroxyphenyl benzotriazole function" is intended to mean any molecule comprising, in its structure at least one —SiO group and at least one 2-hydroxyphenyl benzotriazole group, it being possible for said molecule to be in the form of a simple siloxane or alkoxysilane compound, of an oligosiloxane or of a polysiloxane.

In particular, the siloxane compounds comprising a 2-hydroxyphenyl benzotriazole function, having the following formula (III), are known, with

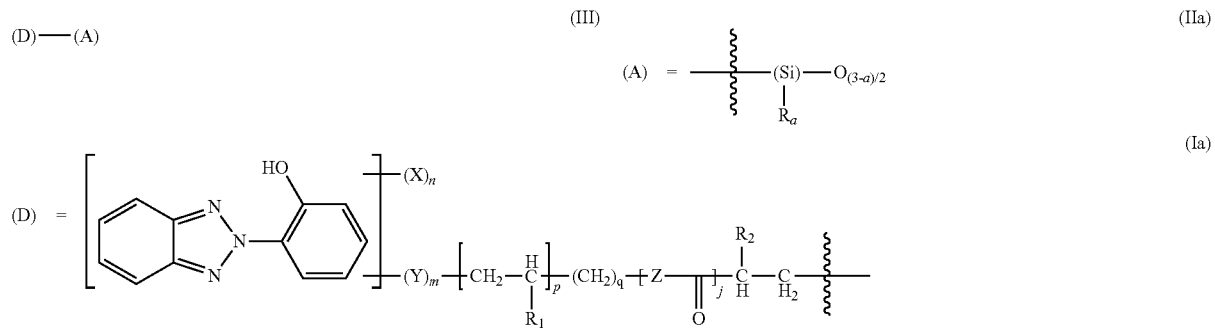

in which the group (A) represents the siloxane part of formula (III) where:

R, which may be identical or different, denote a linear or branched, and optionally halogenated or unsaturated, $C_1$-$C_{30}$ alkyl radical, a $C_6$-$C_{12}$ aryl radical, or a $C_1$-$C_{10}$ alkoxy radical, which may be linear or branched, the group —$OSi(CH_3)_3$;

a is an integer between 0 and 2 inclusive;

and in which the group (D) represents a 2-hydroxyphenyl benzotriazole derivative of formula (Ia) where:

n is an integer between 0 and 3 inclusive;

X, which may be identical or different, are chosen from linear or branched $C_1$-$C_8$ alkyl radicals, halogens and linear or branched $C_1$-$C_4$ alkoxy radicals;

m is 0 or 1;

p is 0 or 1;

q is an integer ranging from 0 to 12;

Y represents —O—, —NH—, —(C=O)O—, —O(CH$_2$)$_v$(C=O)O— or —(CH$_2$)$_w$O(C=O)NH—;

v and w being integers between 0 and 12 inclusive;

Z represents —O— or —NH—;

j is 0 or 1;

$R_1$ represents hydrogen or a linear or branched $C_1$-$C_4$ alkyl radical;

$R_2$ represents hydrogen or a methyl radical.

In addition to the units of formula (A), the organosiloxane may comprise units of formula:

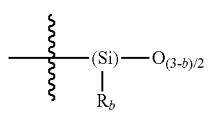

in which:

R has the same meaning as in formula (IIa);

b=1, 2 or 3.

Preferably, the compounds of formula (III) correspond to one of formula (IIIa) or (IIIb) below:

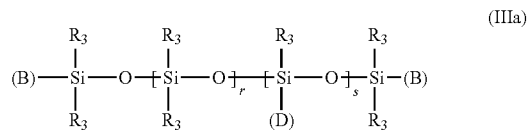

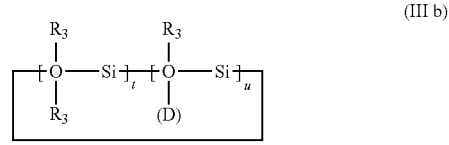

in which:

(D) corresponds to formula (Ia) as defined above, $R_3$, which may be identical or different, are chosen from linear or branched $C_1$-$C_{20}$ alkyl, phenyl, 3,3,3-trifluoropropyl and trimethylsilyloxy radicals or the hydroxyl radical, (B), which may be identical or different, are chosen from the radicals $R_3$ and the group (D), r is an integer between 0 and 200 inclusive, s is an integer ranging from 0 to 50 and, if s=0, at least one of the two symbols (B) denotes (D), u is an integer ranging from 1 to 10, t is an integer ranging from 0 to 10, it being understood that t+u is greater than or equal to 3.

The linear or cyclic diorganosiloxanes of formula (IIIa) or (IIIb) are random oligomers or polymers preferably having at least one, and even more preferably all, of the following characteristics:

$R_3$ is the methyl radical.

The linear diorganosiloxanes of formula (IIIa) are particularly preferred.

By way of examples of compounds of formula (III), which are particularly preferred, use will be made of the compounds having the following formulae (a) to (k):

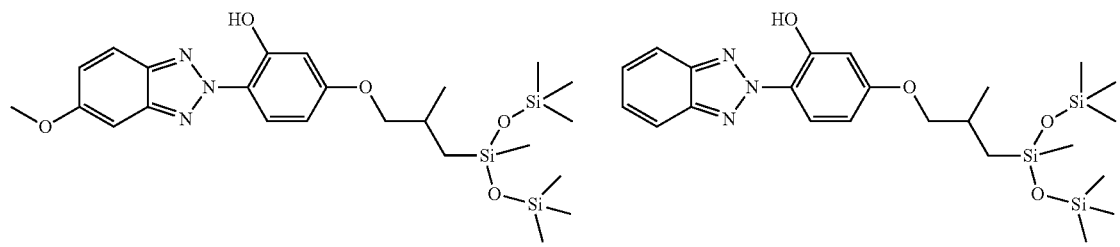

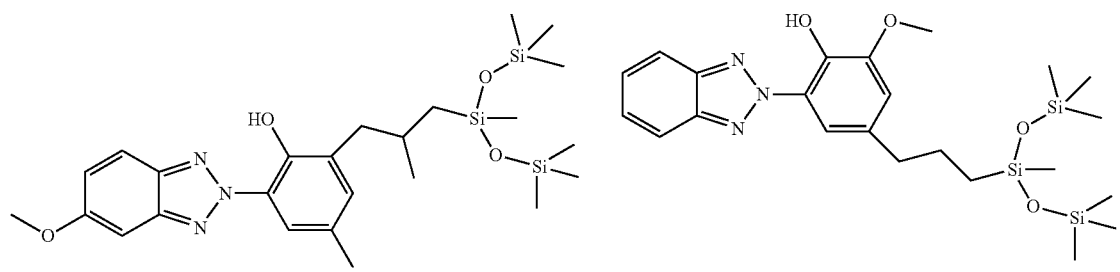

-continued
(e)
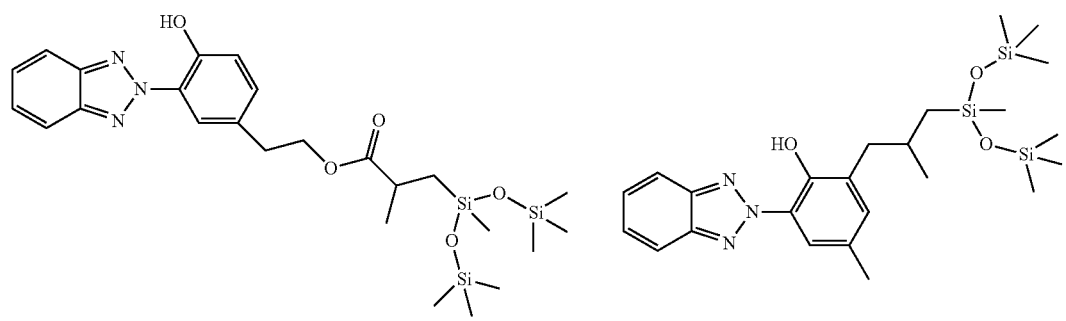
(f)
(g)
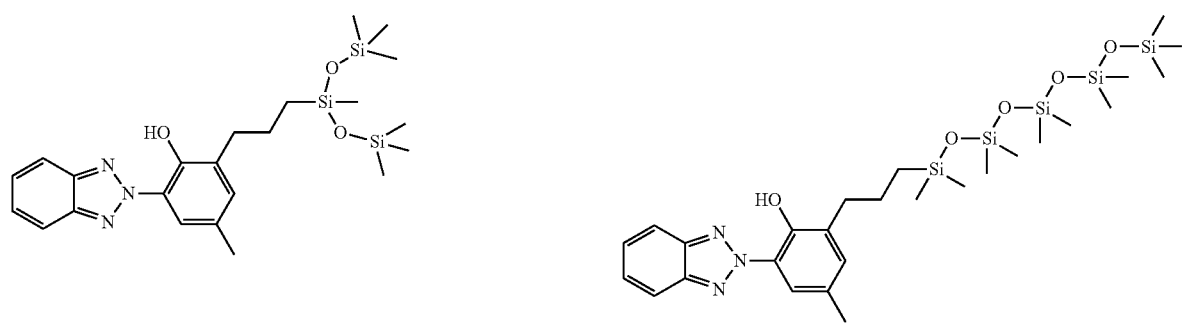
(h)
(i)
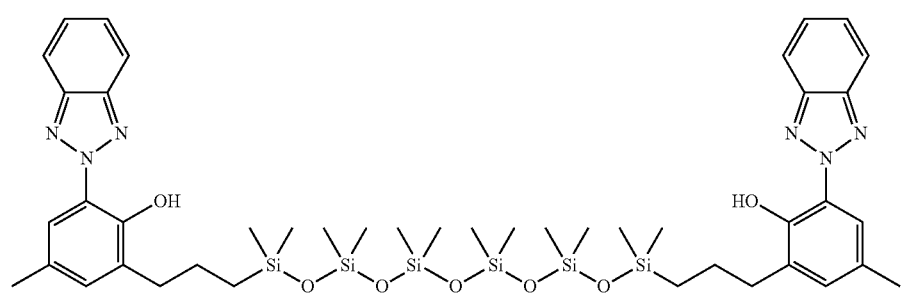
(j)
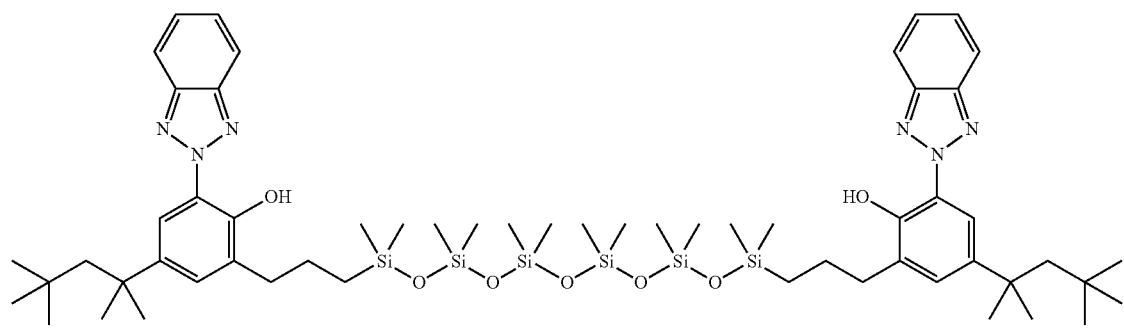

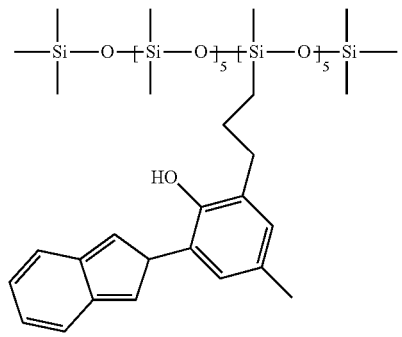

random derivative with r = s = 5

(a)=2-(5-methoxy-2H-1,2,3-benzotriazol-2-yl)-5-(2-methyl-3-{1,3,3,3-tetramethyl-1-[(trimethylsilyl)oxy]disiloxanyl}propoxy)phenol
(b)=2-(2H-1,2,3-benzotriazol-2-yl)-5-(2-methyl-3-{1,3,3,3-tetramethyl-1-[(trimethylsilyl)oxy]disiloxanyl}propoxy)phenol
(c)=2-(5-methoxy-2H-1,2,3-benzotriazol-2-yl)-4-methyl-6-(2-methyl-3-{1,3,3,3-tetramethyl-1-[(trimethylsilyl)oxy]disiloxanyl}propyl)phenol
(d) 2-(2H-1,2,3-benzotriazol-2-yl)-6-methoxy-4-(3-{1,3,3,3-tetramethyl-1-[(trimethylsilyl)oxy]disiloxanyl}propyl)phenol
(e) 2-[3-(2H-1,2,3-benzotriazol-2-yl)-4-hydroxyphenyl]ethyl 2-methyl-3-{1,3,3,3-tetramethyl-1-[(trimethylsilyl)oxy]disiloxanyl}propanoate
(f)=2-(2H-1,2,3-benzotriazol-2-yl)-4-methyl-6-(2-methyl-3-{1,3,3,3-tetramethyl-1-[(trimethylsilyl)oxy]disiloxanyl}propyl)phenol
(g)=2-(2H-1,2,3-benzotriazol-2-yl)-4-methyl-6-(3-{1,3,3,3-tetramethyl-1-[(trimethylsilyl)oxy]disiloxanyl}propyl)phenol
(h)=2-(2H-1,2,3-benzotriazol-2-yl)-4-methyl-6-[3-(undecamethylpentasiloxanyl)propyl]phenol
(i)=2-(2H-1,2,3-benzotriazol-2-yl)-6-[3-(11-{3-[3-(2H-1,2,3-benzotriazol-2-yl)-2-hydroxy-5-methylphenyl]propyl}-1,1,3,3,5,5,7,7,9,9,11,11-dodecamethylhexasiloxanyl)propyl]-4-methylphenol
(j) 2-(2H-1,2,3-benzotriazol-2-yl)-6-[3-(11-{3-[3-(2H-1,2,3-benzotriazol-2-yl)-2-hydroxy-5-(1,1,3,3-tetramethylbutyl)phenyl]propyl}-1,1,3,3,5,5,7,7,9,9,11,11-dodecamethylhexasiloxanyl)propyl]-4-(1,1,3,3-tetramethylbutyl)phenol.

Even more particularly preferred are the derivatives of formula (IIIa) in which r=0, s=1, and (B) is methyl.

Even more preferably, the compound of formula (f) is preferred. This compound is known as Drometrizole Trisiloxane (CTFA name) corresponding to the following formula:

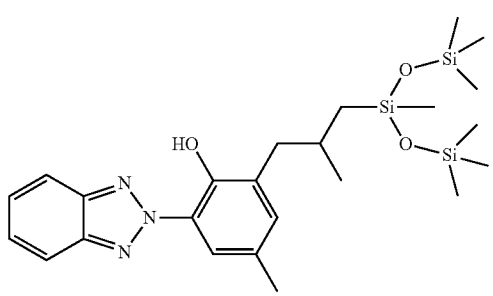

which is a product produced by the company Rhodia under the name Silatrizole.

These siloxane compounds comprising a 2-hydroxyphenyl benzotriazole function and the syntheses thereof have been described in U.S. Pat. Nos. 4,316,033, 4,373,060, EP 0388218, U.S. Pat. No. 5,089,250, EP 0354145, EP 0708108, EP 0711779 and application WO 9406404.

The siloxane compounds comprising a 2-hydroxyphenyl benzotriazole function of formula (III) are obtained, according to these documents, by hydrosilylation reaction of a 2-hydroxyphenyl benzotriazole comprising a substituent comprising a terminal double bond (of formula (I) defined below) with a siloxane compound comprising an SiH function (of formula (II) defined below), in the presence of a suitable catalyst and a suitable solvent (in particular toluene).

In order to prepare the siloxane compounds of formula (III), the compound of 2-hydroxyphenyl benzotriazole of formula (I) below is reacted with a siloxane comprising an SiH function, of formula (II) below:

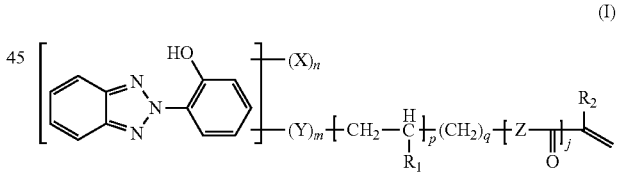

in which $R_1$, $R_2$, X, Y, Z, n, m, p, q and j have the same meaning as in formula (III):

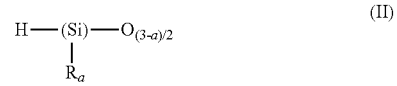

in which R and a have the same meaning as in formula (III), and according to the following reaction scheme A:

SCHEME A

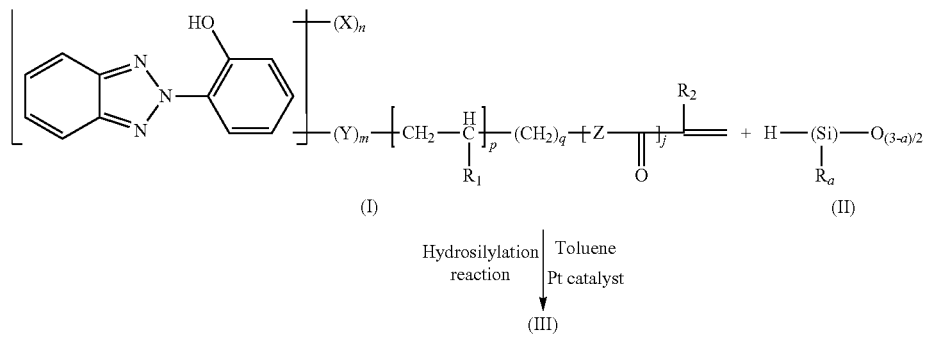

As emerges from formula (Ia) given above, the attachment of the chain unit:

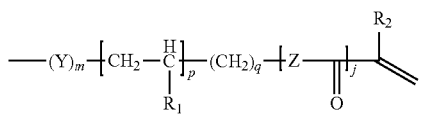

to the 2-hydroxyphenyl benzotriazole unit, which thus connects said 2-hydroxyphenyl benzotriazole unit to the silicon atom of the silicone chain can take place in any of the available positions offered by the two aromatic nuclei of the 2-hydroxyphenyl benzotriazole:

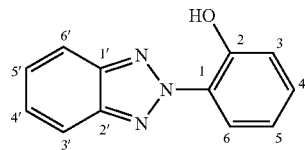 [SMILES: Oc1ccccc1-n1nc2ccccc2n1]

Preferably, this attachment takes place at position 3, 4, 5 (aromatic nucleus bearing the hydroxyl function) or 4' (benzene nucleus adjacent to the triazole ring), and even more preferably at position 3, 4 or 5.

Similarly, the attachment of the substituent unit X can take place in any of the other available positions within the 2-hydroxyphenyl benzotriazole. However, this attachment preferably takes place at position 3, 4, 4', 5 and/or 6.

The 2-hydroxyphenyl benzotriazole derivatives of formula (I), which are starting products in the synthesis of the silicone sunscreens comprising a 2-hydroxyphenyl benzotriazole function, of formula (III), are known per se and the syntheses thereof have been described in patents FR 1325404, U.S. Pat. Nos. 4,316,033, 4,328,346, 4,373,060, GB 2077280, EP 0392883, EP 0708108, EP 0711779 and US 20090270632.

A process for the synthesis of the two derivatives of formula (III), with $R_1=R_2=H$, $p=1$, $q=0$, $m=j=0$, $a=0$, $n=1$, and X (at position 5)=$CH_3$, has been described in U.S. Pat. Nos. 4,316,033 and 4,373,060 according to the following operating conditions: solvent: toluene, Karstedt catalyst (5% solution) at 60° C. for 1 hour. The crude products obtained are oils. Although the crude yields are satisfactory, the amount of catalyst used (1120 ppm Pt relative to the weight of the 2 reactants) makes this process too expensive. In addition, to obtain products having a purity greater than 99%, purification is required, for example on a chromatographic column, and this makes the process economically unattractive.

In patent EP 0388218, the synthesis of derivatives of formula (III) is obtained by reacting a mono or di SiH derivative of formula (V) with the derivatives of formula (I') in which $R'_1$ is hydrogen, a $C_1$-$C_8$ alkyl radical, a $C_1$-$C_8$ alkoxy radical or a halogen, $R'_2$ is hydrogen, a $C_1$-$C_8$ alkyl radical, a $C_1$-$C_8$ alkoxy radical, a carbalkoxy, a hydroxyl radical, an amino radical or a halogen, and $R'_3$ is hydrogen or a $C_1$-$C_8$ alkyl radical, according to the following scheme:

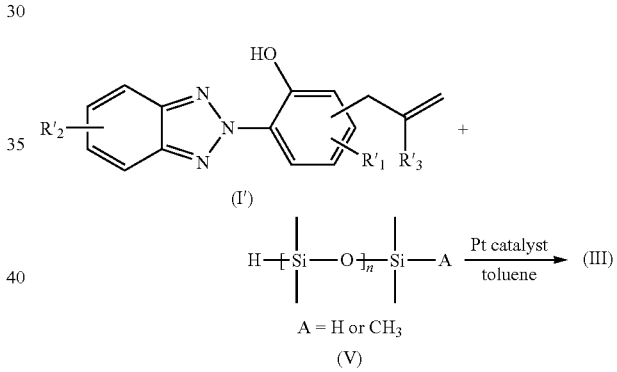

A = H or $CH_3$ (V)

The hydrosilylation reaction is carried out in toluene. The oils mainly obtained are purified by passing over a silica column. In addition, the toluene solvent used in this process is non suitable for environmental or human health.

In U.S. Pat. No. 5,089,250, the synthesis of the derivatives of formula (III) is obtained by reacting a polymer comprising SiH of formula (VI), with the derivatives of formula (I'') in which $R'_1$ is hydrogen or a $C_1$-$C_8$ alkyl radical, $R'_3$ is hydrogen or a $C_1$-$C_4$ alkyl radical and p is an integer between 1 and 10, according to the following scheme:

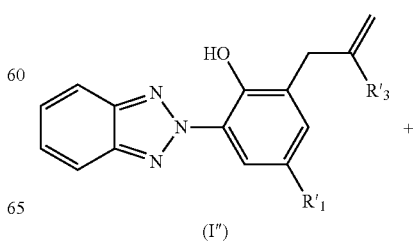

-continued

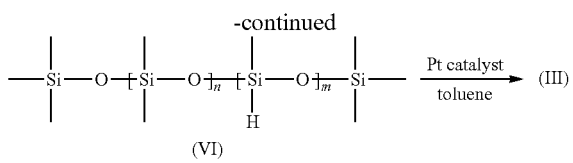
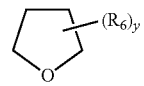

(VI)

The hydrosilylation reaction can be carried out under bulk conditions or in a volatile organic solvent such as toluene, heptane, xylene, tetrahydrofuran and tetrachloroethylene. It is generally desirable to heat the reaction mixture at a temperature of between 60 and 120° C. for the amount of time necessary for the reaction to be complete. The oils mainly obtained are purified by passing over a silica column. While the crude yields obtained are satisfactory, the amounts of platinum catalyst (platinum on carbon at 5%: 120 ppm relative to the weight of the 2 reactants) used remain high and the reaction times for the hydrosilylation reaction to be complete are very long (minimum of 10 hours).

In patent WO 9406404, the synthesis of the derivative of formula (III) with $R_1$=H, p=1, q=0, $R_2$=$CH_3$, m=j=0, a=1, n=1, X (at position 5)=$CH_3$, r=0, s=1, and (B)=$R_3$=$CH_3$ is described with the following operating conditions: solvent: toluene, Karstedt catalyst (Petrarch PC 085, cyclovinylmethylsiloxane complex containing 3-3.5% $Pt^0$) at 60° C. for 1 hour and 15 minutes. Although the amount of catalyst is reasonable, it nevertheless suffers from a yield (yield <80%) which is still insufficient due to an unsatisfactory reactivity in toluene (numerous impurities formed) which makes the isolation more difficult. In addition, the toluene solvent used in this process is a product known for its toxic effects and for its negative impact on the environment.

It is therefore noted that the operating conditions proposed by these synthesis processes are not sufficiently satisfactory to obtain the derivatives of formula (III) with good yields, use of a smaller amount of platinum catalyst, and isolation of product of good quality.

There remains, therefore, a need to find another synthesis process which has a higher performance level in terms of the amount of platinum catalyst to be used, the reaction time and the isolation of the products without the drawbacks encountered with the processes of the prior art.

The Applicant has discovered, surprisingly, that this objective can be achieved by means of a process for preparing a siloxane compound comprising a 2-hydroxyphenyl benzotriazole function of formula (III), which comprises at least one step in which a reaction for hydrosilylation of a compound 2-hydroxyphenyl benzotriazole comprising a substituent having a double bond of formula (I) with a siloxane compound comprising an SiH function is carried out in the presence of a catalyst and of at least one volatile organic solvent corresponding to one of formulae (VII) or (VIII):

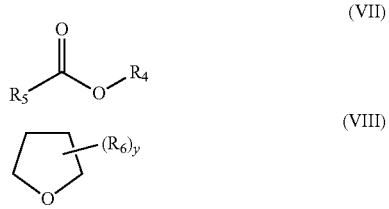

(VII)

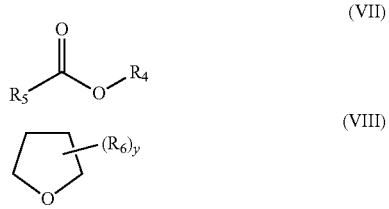

(VIII)

in which $R_4$ and $R_5$, which may be identical or different, represent a linear or branched $C_1$-$C_4$ alkyl radical, with the proviso that the sum of the carbons of $R_4$ and $R_5$ is less than or equal to 6;
y is an integer between 1 and 3;
$R_6$, which may be identical or different, are linear or branched $C_1$-$C_3$ alkyl radicals, with the proviso that the sum of the carbons of $R_6$ are less than or equal to 6.

This discovery forms the basis of the present invention.

The present invention therefore relates to a process for preparing a siloxane compound comprising a benzotriazole function of formula (III), which comprises at least one step in which a reaction for hydrosilylation of a compound 2-hydroxyphenyl benzotriazole comprising a substituent comprising a double bond (of formula (I) with a siloxane compound comprising an SiH function (of formula (II)) is carried out in the presence of a catalyst and of at least one volatile organic solvent corresponding to one of formulae (VII) or (VIII) below:

(VII)

(VIII)

in which $R_4$ and $R_5$, which may be identical or different, represent a linear or branched $C_1$-$C_4$ alkyl radical, with the proviso that the sum of the carbons of $R_4$ and $R_5$ is less than or equal to 6;
y is an integer between 1 and 3;
$R_6$, which may be identical or different, are linear or branched $C_1$-$C_3$ alkyl radicals, with the proviso that the sum of the carbons of $R_6$ is less than or equal to 6.

More particularly, the process in accordance with invention comprises the following steps:

a) the compound 2-hydroxyphenyl benzotriazole comprising a substituent having a terminal double bond of formula (I) is charged, under an inert nitrogen atmosphere, in the presence of at least one volatile organic solvent corresponding to one of formulae (VII) and (VIII);
b) the catalyst is charged to the reaction medium;
c) the reaction medium is heated at a temperature below 100° C.;
d) the siloxane comprising an SiH function of formula (II) is introduced into the reaction medium
e) the reaction medium is heated at a temperature below 150° C. until complete conversion is obtained;
f) purification is carried out.

The present invention relates more particularly to a process for preparing a 2-hydroxyphenyl benzotriazole siloxane compound of the following formula (III):

(D)—(A)  (III)

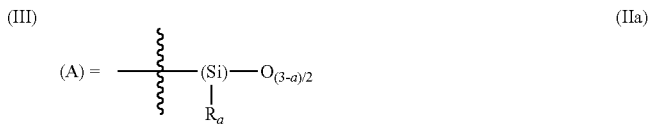

(IIa)

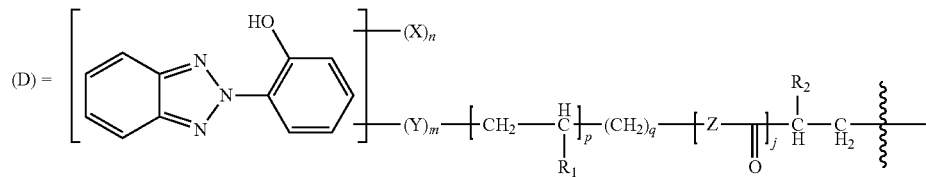

in which the group (A) represents the siloxane part of formula (III) where:

R, which may be identical or different, denote a linear or branched, and optionally halogenated or unsaturated, $C_1$-$C_{30}$ alkyl radical, a $C_6$-$C_{12}$ aryl radical, or a $C_1$-$C_{10}$ alkoxy radical, which may be linear or branched, the group —OSi(CH$_3$)$_3$;

a is an integer between 0 and 2 inclusive;

and in which the group (D) represents the 2-hydroxyphenyl benzotriazole derivatives of formula (Ia) where:

n is an integer between 0 and 3 inclusive;

X, which may be identical or different, are chosen from linear or branched $C_1$-$C_8$ alkyl radicals, halogens and linear or branched $C_1$-$C_4$ alkoxy radicals;

m is 0 or 1;

p is 0 or 1;

q is an integer ranging from 0 to 12;

Y represents —O—, —NH—, —(C=O)O—, —O(CH$_2$)$_v$(C=O)O— or —(CH$_2$)$_w$O(C=O)NH—;

v and w being integers between 0 and 12 inclusive;

Z represents —O— or —NH—;

j is 0 or 1;

$R_1$ represents hydrogen or a linear or branched $C_1$-$C_4$ alkyl radical;

$R_2$ represents hydrogen or a methyl radical.

In addition to the units of formula (A), the organosiloxane may comprise units of formula:

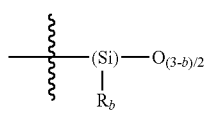

characterized in that it comprises at least one step in which a reaction for hydrosilylation of a 2-hydroxyphenyl benzotriazole derivative of formula (I) below:

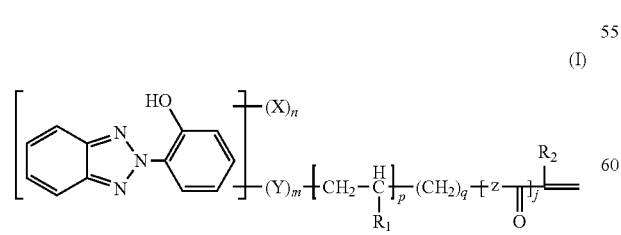

in which $R_1$, $R_2$, X, Y, Z, n, m, p, q and j have the same meaning as in formula (III) with a siloxane compound of formula (II) below:

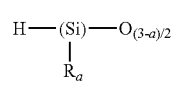

in which R and a have the same meaning as in formula (III); is carried out in the presence of a catalyst and of at least one volatile organic solvent corresponding to formulae (VII) and (VIII) below:

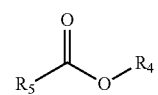

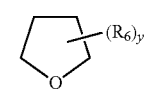

in which $R_4$ and $R_5$, which may be identical or different, represent a linear or branched $C_1$-$C_4$ alkyl radical, with the proviso that the sum of the carbons of $R_4$ and $R_5$ is less than or equal to 6;

y is an integer between 1 and 3;

$R_6$ is a linear or branched $C_1$-$C_3$ alkyl radical, with the proviso that the sum of the carbons of $R_6$ is less than or equal to 6.

The 2-hydroxyphenyl benzotriazole derivatives of formula (I), which are starting products in the synthesis of the 2-hydroxyphenyl benzotriazole siloxane compounds of formula (III) are known per se and the syntheses thereof have been described in FR1325404, U.S. Pat. Nos. 4,316,033, 4,373,060, GB 2077280, EP 0392883 and US 20090270632.

Among 2-hydroxyphenyl benzotriazole derivatives of formula (I) that can be used as starting product in the process of the invention, mention may be made of the following derivatives of formulae (m) to (r):

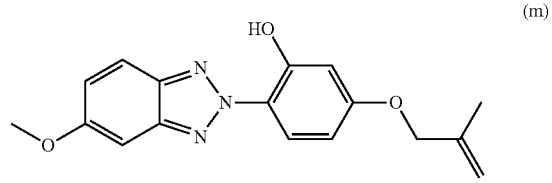

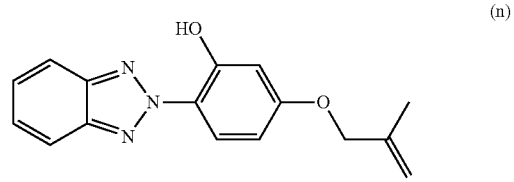

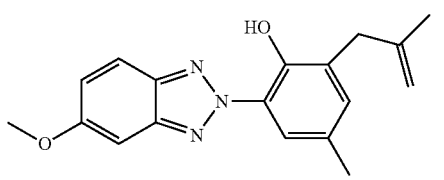

(o)

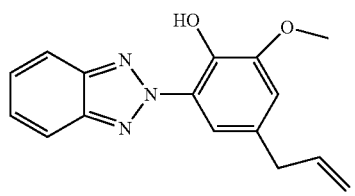

(p)

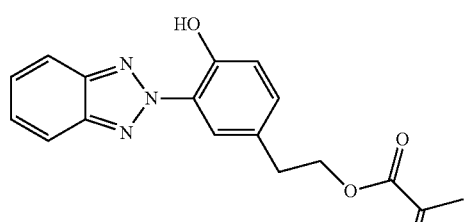

(q)

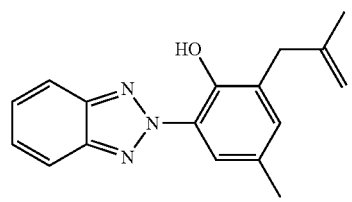

(r)

(m)=2-(5-methoxy-2H-1,2,3-benzotriazol-2-yl)-5-[(2-methylprop-2-enyl)oxy]phenol
(n)=2-(2H-1,2,3-benzotriazol-2-yl)-5-[(2-methylprop-2-enyl)oxy]phenol
(o)=2-(5-methoxy-2H-1,2,3-benzotriazol-2-yl)-4-methyl-6-(2-methylprop-2-enyl)phenol
(p)=4-allyl-2-(2H-1,2,3-benzotriazol-2-yl)-6-methoxyphenol
(q)=2-[3-(2H-1,2,3-benzotriazol-2-yl)-4-hydroxyphenyl] ethyl 2-methylacrylate
(r)=2-(2H-1,2,3-benzotriazol-2-yl)-4-methyl-6-(2-methylprop-2-enyl)phenol Even more preferably, use will be made of the compound 2-(2H-1,2,3-benzotriazol-2-yl)-4-methyl-6-(2-methylprop-2-enyl)phenol of formula (r) below:

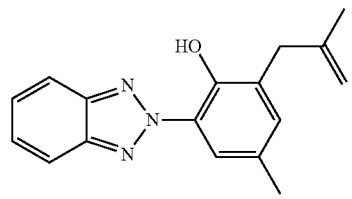

(r)

The SiH comprising siloxane derivatives of formula (II) are products that are well known in the silicone industry and are generally commercially available. They are, for example, described in U.S. Pat. Nos. 3,220,972, 3,697,473 and 4,340,709.

Preferably, use will be made of 1,1,1,3,5,5,5-heptamethyltrisiloxane, diethoxy(methyl)silane, 1,1,1,5,5,5-hexamethyl-3-[(trimethylsilyl)oxy]trisiloxane, triethoxysilane and methoxy(dimethyl)silane. Preference will be given to 1,1,1,3,5,5,5-heptamethyltrisiloxane.

The present invention relates more particularly to a preparation process according to the invention in which Drometrizole Trisiloxane of formula below is prepared:

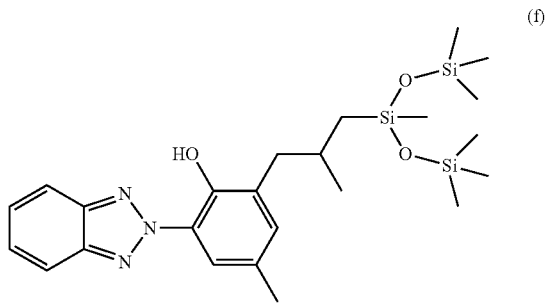 [SMILES: Cc1cc(CC(C)C[Si](C)(O[Si](C)(C)C)O[Si](C)(C)C)c(O)c(-n2nc3ccccc3n2)c1]

(f)

characterized in that it comprises at least the step in which a reaction for hydrosilylation of the compound 2-(2H-1,2,3-benzotriazol-2-yl)-4-methyl-6-(2-methylprop-2-enyl)phenol of formula below:

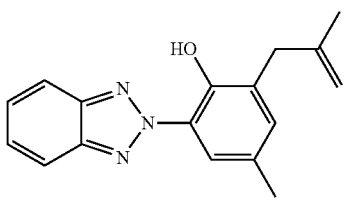

(r)

with the siloxane comprising an SiH function, 1,1,1,3,5,5,heptamethyltrisiloxane, is carried out.

The concentration of the reactants of formulae (I) and (II) in the reaction medium can range between 10% and 90%, and preferably from 20% to 60%.

The siloxane of formula (II) used is placed in a ratio of from 1.0 to 1.5 equivalent relative to the 2-hydroxyphenyl benzotriazole derivative of formula (I), and more preferably from 1.0 to 1.1 equivalents.

The catalysts used for carrying out the reaction for hydrosilylation of the compounds of formula (I) with the derivatives of formula (II) are preferably platinum catalysts and are fully described in the literature. Mention may be made in particular of the platinum-organic product complexes described in U.S. Pat. Nos. 3,159,601, 3,159,602, 3,220,972, EP 0057459, EP 10188978 and EP 0190530, and the platinum-vinylorganopolysiloxane complexes described in U.S. Pat. Nos. 3,419,593, 3,377,432, 3,715,334 and 3,814,730 (Karstedt catalyst). More particularly, Karstedt catalysts such as those provided by the companies Ningbo Fin-chem Co. Ltd, Alfa Aesar, Johnson Matthey and Hereaus will be used.

Among the volatile organic solvents of formula (VII), isopropyl acetate and ethyl acetate will be preferred.

Among the volatile organic solvents of formula (VIII), 2-methyltetrahydrofuran will be preferred.

The temperature of step c) is preferably between 20° C. and 100° C., and more particularly between 30 and 90° C.

The reaction temperature of step e) is preferably between 20° C. and 150° C., and more particularly between 30 and 90° C.

The isolation of the products in step f) can be carried out:
i) either by simple elimination of the solvents (by virtue of their good selectivity in the hydrosilylation reaction, products containing only small amounts of impurities are obtained);
ii) or by elimination of the solvents and recrystallization (in the case of crystallizable products) from a recrystallization solvent which can be chosen from isopropanol or ethanol or binary mixtures ethanol-methanol, isopropanol-methanol, ethanol-isopropanol or ethanol-water, or ternary mixtures isopropanol-methanol-water or isopropanol-ethanol-water. The ternary mixture isopropanol-methanol-water will be preferred;
iii) or in the case of non-recrystallizable products, by simply passing the reaction mixture over a bed containing an adsorbent chosen from active charcoal, zeolites, alumina, silica gels or activated clay. The solvent of the fractions containing the product is thus evaporated off so as to give the final product with a good yield and good purity.

Concrete, but in no way limiting, examples illustrating the invention will now be given.

EXAMPLE 1

Preparation of 2-(2H-1,2,3-benzotriazol-2-yl)-4-methyl-6-{2-methyl-3-{1,3,3,3-tetramethyl-1-[(trimethylsilyl)oxy]disiloxanyl}propyl)phenol in ethyl acetate 2-(2H-1,2,3-benzotriazol-2-yl)-4-methyl-6-(2-methyl-prop-2-enyl) (20 g, 0.0716 mol) and 20 ml of ethyl acetate are charged to a reactor under nitrogen inerting. The medium is stirred and 8.8 mg of Karstedt catalyst (Johnson Matthey titrated at 9.3% of $Pt^0$, i.e. 23 ppm of Pt relative to the weight of the 2 reactants) diluted with 9 ml ethyl acetate are added. The mixture is brought to to 50-60° C. and 1,1,1,3,5,5,5-heptamethyltrisiloxane (16.37 g, 0.0752 mol, i.e. 1.05 equivalents) diluted with 4 ml of ethyl acetate is added dropwise for 30 minutes. After the addition, the medium is refluxed for 5 hours. After reaction, the solvent is evaporated off and is replaced with 28 ml of a mixture of isopropanol/methanol/water in the ratio 2:0.95:0.05. The medium is brought to 65° C. After a slow cooling, the precipitate is filtered off and is washed with a cold mixture of isopropanol/methanol/water in the ratio 1:1.8:0.2. The product after drying is obtained in the form of white crystals (31.62 g, yield 88%, purity >99%).

EXAMPLE 2

Preparation of 2-(2H-1,2,3-benzotriazol-2-yl)-4-methyl-6-(2-methyl-3-{1,3,3,3-tetramethyl-1-[(trimethylsilyl)oxy]disiloxanyl}propyl)phenol in ethyl acetate 2-(2H-1,2,3-benzotriazol-2-yl)-4-methyl-6-(2-methyl-prop-2-enyl) (5 g, 0.0179 mol) and 5 ml of ethyl acetate are charged to a reactor under nitrogen inerting. The medium is stirred and 58 mg of Karstedt catalyst (Ningbo Fin-chem Co. Ltd, grade titrated at 0.3% of $Pt^0$, i.e. 19 ppm of Pt relative to the weight of the 2 reactants) diluted with 2.25 ml of ethyl acetate are added. The mixture is brought to 50-60° C. and 1,1,1,3,5,5,5-heptamethyltrisiloxane (4.09 g, 0.188 mol, i.e. 1.05 equivalents) diluted with 0.25 ml of ethyl acetate is added dropwise for 30 minutes. After the addition, the medium is refluxed. After complete reaction, the solvent is evaporated and is replaced with 7 ml of a mixture of isopropanol/methanol/water in the ratio 2:0.95:0.05. The medium is brought to 65° C. After slow cooling, the precipitate is filtered off and is washed with a cold mixture of isopropanol/methanol/water in the ratio 1:1.8:0.2. The product after drying is obtained in the form of white crystals (8.0 g, yield 89%, purity >99%).

EXAMPLE 3

Preparation of 2-(2H-1,2,3-benzotriazol-2-yl)-4-methyl-6-(2-methyl-3-{1,3,3,3-tetramethyl-1-[(trimethylsilyl)oxy]disiloxanyl}propyl)phenol in 2-methyltetrahydrofuran 2-(2H-1,2,3-benzotriazol-2-yl)-4-methyl-6-(2-methyl-prop-2-enyl) (5 g, 0.0179 mol) and 5 ml of 2-methyltetrahydrofuran are charged to a reactor under nitrogen inerting. The medium is stirred and 58 mg of Karstedt catalyst (Ningbo Fin-chem Co. Ltd, grade titrated at 0.3% of $Pt^0$, i.e. 19 ppm of Pt relative to the weight of the 2 reactants) diluted with 2.25 ml of 2-methyltetrahydrofuran are added. The mixture is brought to 50-60° C. and 1,1,1,3,5,5,5-heptamethyltrisiloxane (4.09 g, 0.188 mol, i.e. 1.05 equivalents) diluted with 0.25 ml of 2-methyltetrahydrofuran is added dropwise for 30 minutes. After the addition, the medium is refluxed.

After complete reaction, the solvent is evaporated and is replaced with 7 ml of a mixture of isopropanol/methanol/water in the ratio 2:0.95:0.05. The medium is brought to 65° C. After slow cooling, the precipitate is filtered off and is washed with a cold mixture of isopropanol/methanol/water in the ratio 1:1.8:0.2. The product after drying is obtained in the form of white crystals (7.82 g, yield 87%, purity >99%).

COUNTEREXAMPLE 1 ACCORDING TO THE PROCESS OF APPLICATION WO9406404

Preparation of 2-(2H-1,2,3-benzotriazol-2-yl)-4-methyl-6-(2-methyl-3-{1,3,3,3-tetramethyl-1-[(trimethylsilyl)oxy]disiloxanyl}propyl)phenol in toluene 2-(2H-1,2,3-benzotriazol-2-yl)-4-methyl-6-(2-methyl-prop-2-enyl) (5 g, 0.0179 mol) and 5 ml of toluene are charged to a reactor under an inert nitrogen atmosphere. The medium is stirred and 58 mg of Karstedt catalyst (Ningbo Fin-chem Co. Ltd, grade titrated at 0.3% of $Pt^0$, i.e. 19 ppm of Pt relative to the weight of the 2 reactants) diluted with 2.25 ml of toluene are added. The mixture is brought to 50-60° C. and 1,1,1,3,5,5,5-heptamethyltrisiloxane (4.09 g, 0.188 mol, i.e. 1.05 equivalents) diluted with 0.25 ml of toluene is added dropwise for 30 minutes. After addition, the medium is refluxed.

After complete reaction, the solvent is evaporated and is replaced with 7 ml of a mixture of isopropanol/methanol/water in the ratio 2:0.95:0.05. The medium is brought to ~65° C. After slow cooling, the precipitate is filtered and is washed with a cold mixture of isopropanol/methanol/water in the ratio 1:1.8:0.2. The product after drying is obtained in the form of white crystals (7.1 g, yield 79%, purity >99%).

With yields of 88%-89%, examples 1 and 2 with ethyl acetate as hydrosilylation reaction solvent, show us that this solvent stands out from that of counterexample 1 (toluene) with a yield of 79%.

The invention claimed is:

1. A process for preparing a siloxane compound comprising a 2-hydroxyphenyl benzotriazole function, the process comprising:

(D)—(A)    (III)

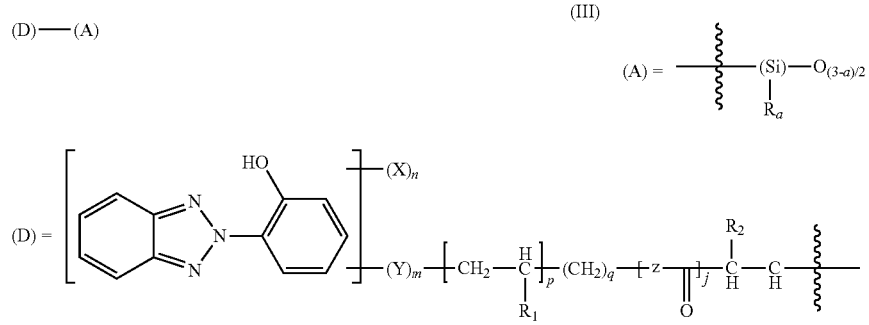

reacting a compound 2-hydroxyphenyl benzotriazole comprising a substituent comprising a terminal double bond with a siloxane compound comprising a SiH function in the presence of a catalyst and at least one volatile organic solvent of formula (VII) and formula (VIII) below:

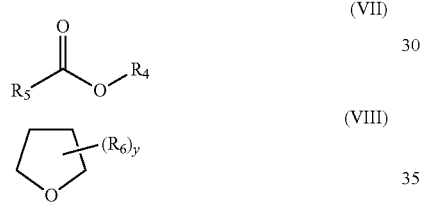

wherein:
$R_4$ and $R_5$ are independently a linear or branched $C_1$-$C_4$ alkyl radical, and a sum of carbons of $R_4$ and $R_5$ is less than or equal to 6;
y is an integer between 1 and 3;
each $R_6$ is independently a linear or branched $C_1$-$C_3$ alkyl radical, and a sum of carbons of $R_6$ is less than or equal to 6.

2. The process according to claim 1, further comprising:
a) charging the compound 2-hydroxyphenyl benzotriazole comprising a substituent comprising a terminal double bond, under an inert nitrogen atmosphere, in the presence of the at least one volatile organic solvent;
b) dissolving and charging the catalyst;
c) heating a reaction medium comprising the compound 2-hydroxyphenyl benzotriazole comprising a substituent comprising a terminal double bond, the at least one volatile organic solvent, and the catalyst at a temperature below 100° C.;
d) adding the siloxane compound comprising a SiH function into the reaction medium so that a reaction mixture comprising the reaction medium and the siloxane compound comprising a SiH function is obtained; and
e) purifying the reaction mixture,
wherein:
the charging a), the dissolving and charging b), the heating c), and the adding d) occur prior to said reacting;
said reacting occurs at a temperature below 150° C. until complete conversion is obtained; and
the purifying e) occurs after said reacting.

3. The process according to claim 1, wherein:

the siloxane compound comprising a 2-hydroxyphenyl benzotriazole function is of formula (III) below:

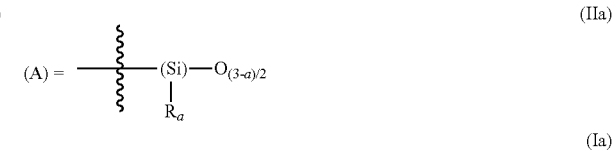

wherein:
group (A) is a silicone part of the formula (III)
wherein:
each R, is independently a linear or branched, optionally halogenated or unsaturated, $C_1$-$C_{30}$ alkyl radical, a $C_6$-$C_{12}$ aryl radical, a linear or branched $C_1$-$C_{10}$ alkoxy radical or a —OSi(CH$_3$)$_3$ group; and
a is an integer of from 0 to 2;
group (D) is a 2-hydroxyphenyl benzotriazole derivative of formula (Ia)
wherein:
n is an integer of from 0 to 3;
each X is independently selected from the group consisting of a linear or branched $C_1$-$C_8$ alkyl radical, a halogen and a linear or branched $C_1$-$C_4$ alkoxy radical;
m is 0 or 1;
p is 0 or 1;
q is an integer of from 0 to 12;
Y is —O—, —NH—, —(C=O)O—, —O(CH$_2$)$_v$(C=O)O—, or —(CH$_2$)$_w$O(C=O)NH—;
v and w are integers of from 0 to 12;
Z is —O— or —NH—;
j is 0 or 1;
$R_1$ is hydrogen or a $C_1$-$C_4$ alkyl radical; and
$R_2$ is hydrogen or a methyl radical;
the siloxane compound comprising a 2-hydroxyphenyl benzotriazole function optionally further comprises group of formula:

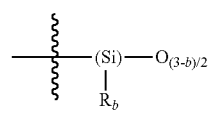

wherein:
b is an integer of 1, 2 or 3;
the compound 2-hydroxyphenyl benzotriazole comprising a substituent comprising a terminal double bond is of formula (I) below:

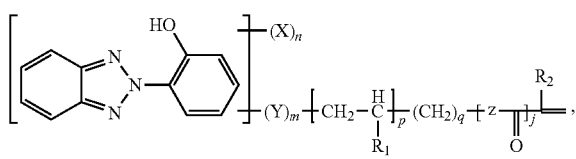

and
the siloxane compound comprising a SiH function is of formula (II) below:

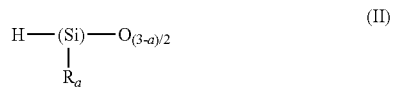

4. The process according to claim 1, wherein the compound 2-hydroxyphenyl benzotriazole comprising a substituent comprising a terminal double bond is selected from the group consisting of:
 a 2-(5-methoxy-2H-1,2,3-benzotriazol-2-yl)-5-[(2-methylprop-2-enyl)oxy]phenol,
 a 2-(2H-1,2,3-benzotriazol-2-yl)-5-[(2-methylprop-2-enyl)oxy]phenol,
 a 2-(5-methoxy-2H-1,2,3-benzotriazol-2-yl)-4-methyl-6-(2-methylprop-2-enyl)phenol,
 a 4-allyl-2-(2H-1,2,3-benzotriazol-2-yl)-6-methoxyphenol,
 a 2-[3-(2H-1,2,3-benzotriazol-2-yl)-4-hydroxyphenyl] ethyl 2-methylacrylate, and
 a 2-(2H-1,2,3-benzotriazol-2-yl)-4-methyl-6-(2-methylprop-2-enyl)phenol.

5. The process according to claim 3, wherein the compound 2-hydroxyphenyl benzotriazole comprising a substituent comprising a terminal double bond of formula (I) is 2-(2H-1,2,3-benzotriazol-2-yl)-4-methyl-6-(2-methylprop-2-enyl)phenol.

6. The process according to claim 1, wherein the siloxane compound comprising a SiH function is selected from the group consisting of a 1,1,1,3,5,5,5-heptamethyltrisiloxane, a diethoxy(methyl)silane, a 1,1,1,5,5,5-hexamethyl-3-[(trimethylsilyl)oxy]trisiloxane, a triethoxysilane and a methoxy(dimethyl)silane.

7. The process according to claim 6, wherein the siloxane compound comprising a SiH function is 1,1,1,3,5,5,5-heptamethyltrisiloxane.

8. The process according to claim 1, wherein a concentration of the siloxane compound comprising a SiH function in a reaction medium comprising the compound 2-hydroxyphenyl benzotriazole comprising a substituent comprising a terminal double bond is between 10% and 90% by weight.

9. The process according to claim 1, wherein the siloxane compound comprising a SiH function is placed in a ratio from 1.0 to 1.5 equivalents relative to the compound 2-hydroxyphenyl benzotriazole comprising a substituent comprising a terminal double bond.

10. The process according to claim 1, wherein the volatile organic solvent of formula (VII) is isopropyl acetate or ethyl acetate.

11. The process according to claim 1, wherein the volatile organic solvent of formula (VIII) is 2-méthyltetrahydrofuran.

12. The process according to claim 2, wherein in the heating c), the reaction medium is heated at a temperature of between 20 and 100° C.

13. The process according to claim 2, wherein said reacting occurs at a temperature of between 20 and 150° C.

14. The process according to claim 2, wherein a recrystallization solvent is used in the purifying e) and the recrystallization solvent is selected from the group consisting of an isopropanol, an ethanol, a binary mixture of ethanol-methanol, a binary mixture of isopropanol-methanol, a binary mixture of ethanol-isopropanol, a binary mixture of ethanol-water, a ternary mixture of isopropanol-methanol-water, and a ternary mixture of isopropanol-ethanol-water.

15. The process according to claim 14, wherein the recrystallization solvent is a ternary mixture of isopropanol-methanol-water.

16. The process according to claim 1, wherein:
 the siloxane compound comprising a 2-hydroxyphenyl benzotriazole function is Drometrizole Trisiloxane of formula (f) below:

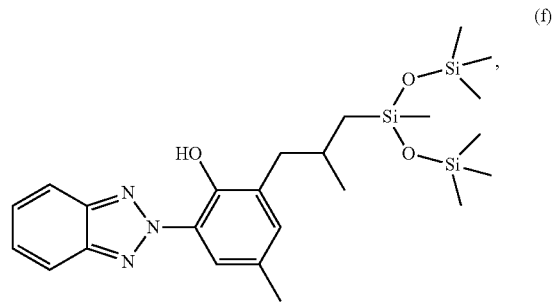 [SMILES: Cc1cc(CC(C)C[Si](C)(O[Si](C)(C)C)O[Si](C)(C)C)c(O)c(-n2nc3ccccc3n2)c1]

the compound 2-hydroxyphenyl benzotriazole comprising a substituent comprising a terminal double bond is 2-(2H-1,2,3-benzotriazol-2-yl)-4-methyl-6-(2-methylprop-2-enyl)phenol of formula (r) below:

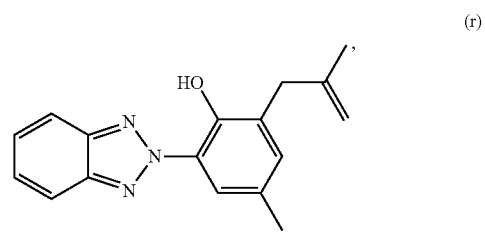 [SMILES: C=C(C)Cc1cc(C)cc(-n2nc3ccccc3n2)c1O]

and
 the siloxane comprising a SiH function is 1,1,1,3,5,5,5-heptamethyltrisiloxane.

17. The process according to claim 1, wherein a concentration of the siloxane compound comprising a SiH function in a reaction medium comprising the compound 2-hydroxyphenyl benzotriazole comprising a substituent comprising a terminal double bond is between 20% and 60% by weight.

18. The process according to claim 1, wherein the siloxane compound comprising a SiH function is placed in a ratio from 1.0 to 1.1 equivalents relative to the compound 2-hydroxyphenyl benzotriazole comprising a substituent comprising a terminal double bond.

19. The process according to claim 2, wherein in the heating c), the reaction medium is heated at a temperature of between 30 and 90° C.

20. The process according to claim 2, wherein said reacting occurs at a temperature of between 30 and 90° C.

* * * * *